US006335200B1

(12) United States Patent
Tiru et al.

(10) Patent No.: US 6,335,200 B1
(45) Date of Patent: Jan. 1, 2002

(54) DEVICE CONTAINING AND METHOD OF MAKING A COMPOSITION HAVING AN ELEVATED FREEZING POINT AND CHANGE OF COLOR AT SELECTED TEMPERATURES

(75) Inventors: Mandayam Osuri Tiru; Maj-Britt Igegred Tiru, both of Jarfalla (SE)

(73) Assignee: Tima AB, Järfälla (SE)

(*) Notice: Subject to any disclaimer, the term of this patent is extended or adjusted under 35 U.S.C. 154(b) by 0 days.

(21) Appl. No.: 09/722,384

(22) Filed: Nov. 28, 2000

Related U.S. Application Data

(63) Continuation of application No. PCT/SE99/00988, filed on Jun. 9, 1999.

(51) Int. Cl.[7] .............................................. G01N 33/12
(52) U.S. Cl. ............................ 436/7; 436/2; 436/164; 436/166; 422/61; 426/232; 116/206; 252/962
(58) Field of Search ...................... 422/61, 102, 103; 436/1, 2, 7, 164, 166; 116/206, 207; 426/231–232; 252/962, 963

(56) References Cited

U.S. PATENT DOCUMENTS

| 2,195,395 A | | 4/1940 | Chapman |
| 2,261,473 A | | 11/1941 | Jennings |
| 4,147,852 A | | 4/1979 | Bozelli et al. |
| 4,154,107 A | * | 5/1979 | Giezen et al. ................. 73/356 |
| 5,053,339 A | * | 10/1991 | Patel .............................. 436/2 |
| 5,182,212 A | * | 1/1993 | Jalinski ......................... 436/2 |
| 5,239,942 A | | 8/1993 | Ignacio et al. |
| 5,306,466 A | * | 4/1994 | Goldsmith .................... 422/58 |

OTHER PUBLICATIONS

International Search Report for corresponding PCT application No. PCT/SE99/00988.

* cited by examiner

Primary Examiner—Lyle A. Alexander
(74) Attorney, Agent, or Firm—Finnegan, Henderson, Farabow, Garrett & Dunner, L.L.P.

(57) ABSTRACT

Composition containing two components, which together show an elevated freezing point and bring about a color change at selected temperatures and method of making the same. Use of the composition to prepare a temperature indicating device by filling the same in a suitable transparent container and with a background in the form of a color, a number or a letter, which facilitates to visually observe the difference in color change.

13 Claims, 1 Drawing Sheet

Figure
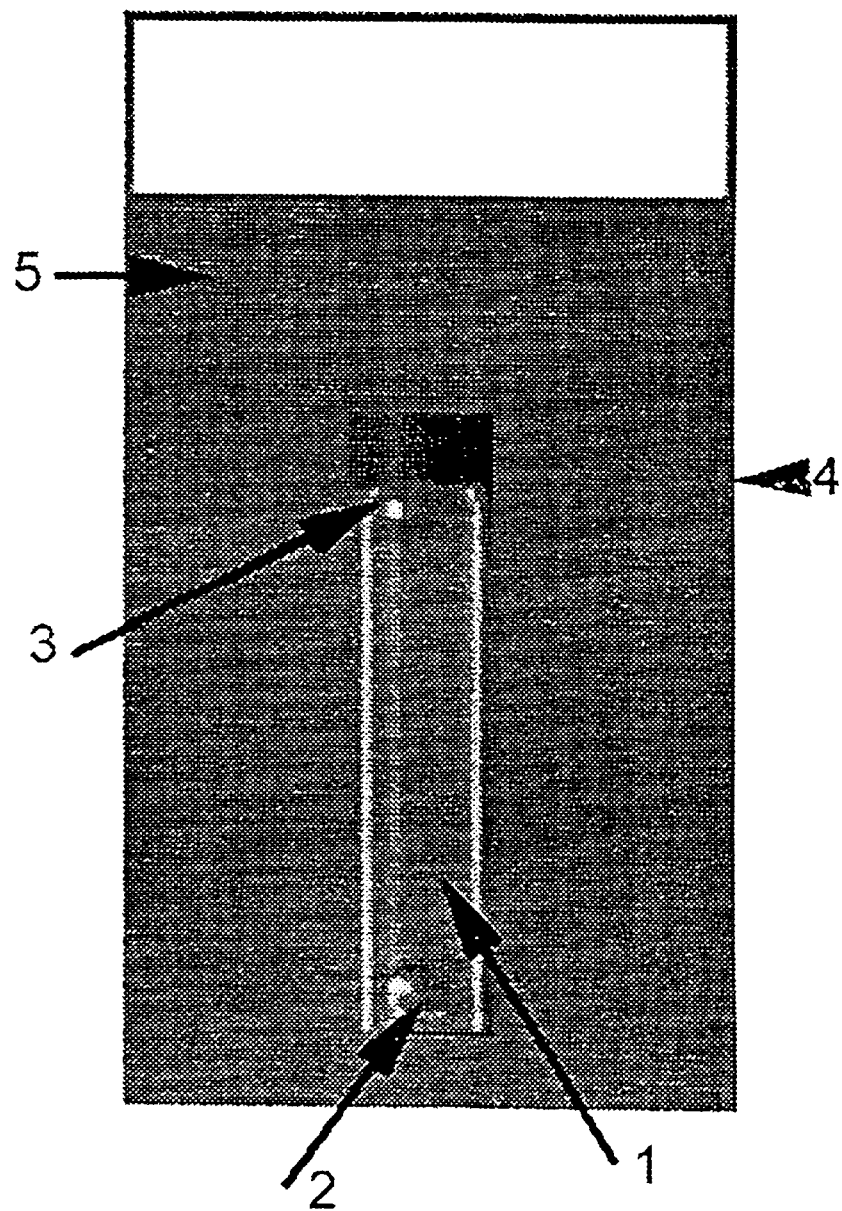

10 # DEVICE CONTAINING AND METHOD OF MAKING A COMPOSITION HAVING AN ELEVATED FREEZING POINT AND CHANGE OF COLOR AT SELECTED TEMPERATURES

CROSS-REFERENCE TO RELATED APPLICATION

This application is a continuation of International Application No. PCT/SE99/00988, filed Jun.9,1999, and Swedish Application No. 9802036-5, filed Jun. 9, 1998. The entire disclosure of each of these applications is relied upon and incorporated by reference herein.

BACKGROUND OF THE INVENTION

The following invention relates in general to a pH-indicator composition consisting of two components, which together show an elevated freezing point and effect a color change at selected freezing temperatures, and to a method of making such a composition. More specifically, the invention aims to utilize such color change, as per the chosen methods, to obtain new compositions for temperature indication, especially down to $-25°$ C. or lower. The field of application for the invention is many, for example, different temperature indicators that can guard temperature-sensitive cold storage or frozen products.

A number of materials, such as finished solutions of pharmaceuticals, vaccines, blood products, chemical products, food products, flowers, etc., can be damaged upon freezing. According to the present invention, a freeze-warning composition can give an early visual warning by color change. In this way, one may easily take steps for corrective action before freezing damages them.

It is generally known that ice packs are used to maintain the cold temperature of cold- storage products during transportation. Usually, ice packs are stored in freezers at $-18°$ C. or lower and placed together with temperature-sensitive cold storage products, such as vaccines or other pharmaceuticals. Sometimes, freeze-sensitive cold storage products are affected because the ice packs have been too cold. In a WHO investigation (WHO/EPI/CCIS/83.7) concerning vaccine transportation, it was observed that between 7.4 and 10.6 per cent of vaccines were damaged by freezing. The WHO recommended that ice packs, after being taken out from the freezer, should be stored at room temperature for sometime before packing together with vaccines. The intention was to raise the temperature of the ice packs to around $-5°$ C. so those freeze-sensitive products were not exposed to freezing risk.

Unnecessary energy is spent to freeze the liquid in the ice packs to $-18°$ C. or lower and afterwards warming them up to between $-4°$ C. or $-5°$ C. before usage. The $-4°$ C. indicators (based on U.S. Pat. No. 4,147,852) which the WHO tested, did not freeze or change color until they were initially exposed to a temperature of $-10°$ C. or lower. Here, our invention can be applied.

The problem has been that temperature indicators that contain salt solutions and are enclosed in sealed glass tubes or plastic packets do not freeze readily. Not before the temperature is lowered too far below the freezing point does a change occur. In addition, the contents in these packages freeze irregularly and with broad temperature intervals, often between $-6°$ C. and $-12°$ C. WHO:s investigation (WHO Weekly Epid. Rec. Nos.50 and 51, 1980) did show that vaccine preparations freeze under a wide interval between $-5°$ C. and $-10°$ C. To solve the problem, a composition according to the present invention can be advantageously applied. This can give an early visual indication that risk for freezing is impending. In principle, pH-indicators represent acid-base character, where the acid side has another color than the basic. One has used this property in acid-base titrations and to prepare temperature dependent indicators based on color change.

U.S. Pat. No. 2,261,473 describes that certain organic or inorganic substances change their acid-base character upon melting or solidification as a result of intramolecular rearrangement. These changes can influence the color of pH indicators, which change reversibly from acid to base color or vice versa.

U.S. Pat. No. 2,195,395 describes a method to show color changes of pH-indicators irreversibly. To the composition is added ester compounds, which at selected temperatures, decompose to acid and alcohol. This is shown by color change.

U.S. Pat. No. 4,147,852 describes a method for regulating color changes of pH-indicators in an aqueous solution at temperatures far below the freezing point. This is made possible by adding certain regulating agents. In the presence of these regulating agents, the composition maintains its color without changing upon freezing. Color change occurs far below the freezing point depending upon the concentration of the added regulatory agent. In such a manner an extended temperature interval between freezing and color change is made possible. In the same patent document are also described results of certain experiments without the addition of regulating agents. Color change was observed upon exposition to between $-18°$ C. and $-20°$ C., i.e. far below the compositions' freezing points. Without having tested if color change takes place at the freezing point itself, one concluded that color change occurred in association with or solely upon freezing (solidification) in analogy with the description in U.S. Pat. No. 2,261,473.

SUMMARY OF THE INVENTION

We have in the present invention established that color change does not occur when buffer solutions containing pH-indicators freeze. The pH-values of the buffer solutions, molarity and ionic strength influence the temperature interval between the freezing point and change of color. Therefore, it is not obvious that color change occurs solely upon freezing.

Accordingly, this invention provides a composition comprising two components. Which together show an elevated freezing point and bring about color change at selected freeze temperatures, wherein the composition comprises as Component 1 a buffer solution containing at least one pH indicator, and as Component 2 at least a solid material in the form of a metal object, which hastens freezing and color change.

In another embodiment of the invention, a composition of the invention comprises two components, which together show an elevated freezing point of a salt solution and brings about a color change at selected temperatures below the freezing point in a reversible way. The composition comprises a first component of a buffer salt solution containing at least one pH indicator, and as a second component, at least one water insoluble solid material that hastens freezing.

In a further embodiment the invention provides a composition comprising two components, which together show an elevated freezing point of a salt solution and shows, by color change, when a selected temperature below freezing is above or below this level. The composition comprises a first component of a buffer salt solution containing at least one pH indicator, and as a second component, at least one water insoluble solid material that hastens freezing.

In a preferred embodiment of the invention, the insoluble material that hastens freezing is a metal ball.

BRIEF DESCRIPTION OF THE DRAWING

This invention will be described in greater detail with reference to the drawing in which:

The FIGURE depicts a freeze warning device containing the composition of this invention.

DETAILED DESCRIPTION OF THE INVENTION

The principles of the invention are discernable from the following description and patent claims.

In the present invention a number of materials have been studied as to their influence on the temperatures of buffer solutions containing pH-indicators upon freezing and change of color. It was observed that the solution's freezing temperature is influenced by additives such that a change occurs at a higher temperature with the additives. Some added materials have been shown to hasten freezing, but not so readily influencing the color change. As is evident from the Examples hereinafter, a metal ball was found to have positive influence on both freezing and color change. This occurred in a way not observed by other added materials. From the Examples, it is also evident that a quicker and distinct color change occurs, especially in the presence of these balls when the temperature is stepwise lowered below 0° C. This is made possible for the product "freeze warning device".

Since the invention aims to use the metal ball in the production of "freeze warning" devices on a large scale, it was deemed necessary that several units of the same composition be tested in order to be certain that the same color change phenomenon occurred within an established temperature interval below freezing point. This is also confirmed in the Examples.

The practical way to exercise the invention is to fill the composition in a suitable transparent container of for example, plastic or glass and against a background of for example, a color, a number or a letter, which facilitates visual reading of color change. The use of container materials that retard heat transfer should be avoided. For this reason, glass containers are preferred, although plastic containers, particularly containers comprised of thin films having good heat transfer properties can be employed. Glass containers having polyethylene stoppers have been found to be suitable. It may also be desirable to hermetically seal the container. In any event, it is not necessary to employ containers having frangible or breakable membranes as in prior art devices.

The FIGURE shows an example of a product "freeze warning device" of this invention. The composition consists of Component 1 according to what is described in Example 1 and the color is blue. Component 2 is a metal ball of 3-mm diameter compatible for use in the test vial 3. The test vial is mounted on a blister package 4 with blue background 5. When the contents of the vial 3 upon freezing change to yellow color, it is easy to read this against the blue background.

There are also products to monitor, which should not thaw. There, the frozen composition according to the invention can be used to warn against thawing,. In one Example (Example 6), there is shown a composition, which upon freezing, changed color from blue to yellow, but it maintained the same yellow color up to −3° C. At −2° C. the color changed to blue. It was discovered that when the temperature was diminished to −3° C. the color changed back to yellow. The composition was still in the frozen state. Thus if it is on the way to thaw, it is easy to read that by observing the color changing to blue.

Deep frozen products should be stored at least at −18° C. An indicator that changes color when the temperature is higher than −18° C. can be made through the use of, for example, a composition where Component 1 contains 0.012 M phosphate buffer of pH 9.9 and with phenolphthalein as pH-indicator (Example 7).

It will be evident from this description and the Examples that the composition of this invention is capable of exhibiting a reversible color change. That is, the color change that occurs following freezing of the composition can be reversed so that the original color of the composition returns by raising the temperature of the frozen composition. Even in this case, reversal of color is observed while the composition is still in a frozen state.

Acid-base indicators are essentially weak acids or bases that exhibit a change of color on the conversion of the acidic form to the basic form, or vice versa. The color change is not a sudden event, but instead the concentrations of the colored forms may change continuously. There exists for each indicator a region or interval of pH above and below which one or the other of the indicator color forms is present in negligibly small concentration. For practical purposes, the width of this transformation range is determined by the sensitivity of the human eye or of the colorimeter used to detect one color in the presence of the other. For visual color comparisons with the unaided eye, the transformation range is typically about 2 pH units wide. This invention can be carried out with a wide variety of such indicators. The sulfonphthalein indicators, which are listed in Table A, have two color transformations and can be employed in this invention.

TABLE A

Sulfonphthalein Indicators

| Indicator | Transformation Range pH | Color Change Acid. Alk. |
|---|---|---|
| Metacresol purple | 1.2–2.8 | Red-yellow |
| Thymol blue | 1.2–2.8 | Red-yellow |
| Bromophenol blue | 3.0–4.6 | Yellow-blue |
| Bromocresol green | 3.8–5.4 | Yellow-blue |
| Chlorophenol red | 5.2–6.8 | Yellow-red |
| Bromophenol red | 5.2–6.8 | Yellow-red |
| Bromophenol purple | 5.2–6.8 | Yellow-purple |
| Bromothymol blue | 6.0–7.6 | Yellow-blue |
| Phenol red | 6.8–8.4 | Yellow-red |
| Cresol red | 7.2–8.8 | Yellow-red |
| Metacresol purple | 7.6–9.2 | Yellow-purple |
| Thymol blue | 8.0–9.6 | Yellow-blue |

Examples of other indicators for use in this invention are given in Table B.

TABLE B

Other Indicators

| Indicator | Transformation Range, pH | Color Change |
|---|---|---|
| o-Cresol red (acid range) | 0.2–1.8 | Red-yellow |
| Thymol blue (acid range) | 1.2–2.8 | Red-yellow |
| Pentamethoxy red | 1.2–3.2 | Red violet-colorless |
| Tropeolin 00 | 1.3–3.2 | Red-yellow |
| 2,4-Dinitrophenol | 2.4–4.0 | Colorless-yellow |
| Methyl yellow | 2.9–4.0 | Red-yellow |
| Methyl orange | 3.1–4.4 | Red-orange |
| Tetrabromophenol blue | 3.0–4.6 | Yellow-blue |
| Alizarin sodium sulfonate | 3.7–5.2 | Yellow-violet |
| α-Naphtylred | 3.7–5.0 | Red-yellow |
| p-Ethoxychrysoidine | 3.5–5.5 | Red-yellow |
| Methyl red | 4.4–6.2 | Red-yellow |
| Bromocresol purple | 5.2–6.8 | Yellow-purple |
| p-Nitrophenol | 5.0–7.0 | Colorless-yellow |
| Azolitmin | 5.0–8.0 | Red-blue |
| Neutral red | 6.8–8.0 | Red-yellow |
| Rosolic acid | 6.8–8.0 | Yellow-red |
| α-Naphtholphthalein | 7.3–8.7 | Rose-green |
| Tropeolin 000 | 7.6–8.9 | Yellow-rose red |
| Phenolphthalein | 8.0–10.0 | Colorless-red |
| α-Naphtholbenzein | 9.0–11.0 | Yellow-blue |
| Thymolphthalein | 9.4–10.6 | Colorless-blue |
| Nile blue | 10.1–11.1 | Blue-red |
| Alizarin yellow | 10.0–12.0 | Yellow-lilac |
| Salicyl yellow | 10.0–12.0 | Yellow-orange brown |
| Diazo violet | 10.1–12.0 | Yellow-violet |
| Tropeolin 0 | 11.0–13.0 | Yellow-orange brown |
| Nitramine | 11.0–13.0 | Colorless-orange brown |
| Poirrier's blue | 11.0–13.0 | Blue violet-pink |
| Trinitrobenzoic acid (indicator salt) | 12.0–13.4 | Colorless-orange red |

Indicator solutions are available commercially, together with equipment (comparators, color charts, and artificial color standards) suitable for visual color matching with the aid of reference buffer solutions. Examples of commercially available indicators are given in Table C.

TABLE C

Commercially Available Indicators

| Indicator | Range, pH | Color Change |
|---|---|---|
| Acid cresol red | 0.2–1.8 | Red-yellow |
| Acid metacresol purple | 1.2–2.8 | Red-yellow |
| Acid thymol blue | 1.2–2.8 | Red-yellow |
| Bromophenol blue | 3.0–4.6 | Yellow-blue |
| Bromocresol green | 3.8–5.4 | Yellow-blue |
| Methyl red | 4.4–6.0 | Red-yellow |
| Chlorophenol red | 5.2–6.8 | Yellow-red |
| Bromocresol purple | 5.2–6.8 | Yellow-purple |
| Bromothymol blue | 6.0–7.6 | Yellow-blue |
| Phenol red | 6.8–8.4 | Yellow-red |
| Cresol red | 7.2–8.8 | Yellow-red |
| Metacresol purple | 7.6–9.2 | Yellow-purple |
| Thymol blue | 8.0–9.6 | Yellow-blue |
| Phthalein red | 8.6–10.2 | Yellow-red |
| Tolyl red | 10.0–11.6 | Red-yellow |
| Acyl red | 10.0–11.6 | Red-yellow |
| Parazo orange | 11.0–12.6 | Yellow-orange |
| Acyl blue | 12.0–13.6 | Red-blue |
| Benzo yellow | 2.4–4.0 | Red-yellow |
| Benzo red | 4.4–7.6 | Red-blue |
| Thymol red | 8.0–11.2 | Yellow-red |
| Long-range indicator | 3.0–11.0 | Red-violet |

These indictors can also be employed in practicing this invention.

In addition, mixed indicators can be employed in the invention. Specifically, for acid-base titrations and for certain other specialized applications indicators with a transformation point are often useful. The so-called "mixed indicators," consisting of an acid-base indicator and a suitable dye, have been developed to meet this need. A familiar example is the methyl orange-xylene cyanole mixture, which has an easily detectable and sharp point of transformation at pH 3.8. The improvement in the sharpness results from the superposition of the (pH dependent) color of the indicator and the color of the dye. Another typical mixed indicator consists of a solution of 1 per cent phenolphthalein and 0.2 per cent methyl green.

Mixtures of two acid-base indicators extend the pH range that can be covered by a single indicator test solution. Such mixed indicators also can be employed in this invention.

This invention can also be carried out with "one-color" indicators, only one form of which (usually the alkaline species) absorbs light in the visible region of the spectrum. Examples of one-color indicators are listed in Table D, together with their colors and transformation ranges.

TABLE D

One-Color Indicators (Acid form colorless)

| Name | Transformation Range, pH | Alkaline color |
|---|---|---|
| Picric acid | 0.1–1.3 | Yellow |
| 2,6-Dinitrophenol | 1.7–4.4 | Yellow |
| 2,4-Dinitrophenol | 2.4–4.0 | Yellow |
| 2,5-Dinitrophenol | 4.0–5.8 | Yellow |
| p-Nitrophenol | 5.3–7.6 | Yellow |
| m-Nitrophenol | 6.4–8.8 | Yellow |
| Phenolphthalein | 8.2–9.8 | Red |
| Salicyl yellow | 10.0–12.0 | Yellow |

In general, about 0.008% to about 0.032% (w/v) of the pH indicator in the test solution (or reference buffer solution) is sufficient for a color change upon freezing of the test solution. Use of the pH indicator at a concentration of about 0.016% (w/v) was found to be acceptable in the Examples. When the indicator itself is only slightly soluble in water, it is often convenient to utilize the water-soluble salt form. The amount of the pH indicator employed should be sufficient for a visible color change with the unaided eye when the composition of the invention is frozen. There does not appear to be an advantage in using large excesses of the pH indicator to enhance performance of the composition or the freeze-thaw device of the invention.

In general, the composition of this invention will have a pH of about 4.5 to about 10. The pH indicator and buffer solution are matched to the pH desired for the composition of the invention. The pH of the composition can, in turn, be selected based upon the pH of the material being monitored for freezing or thawing. For example, if a biological material having a pH of about 6 to about 9 is to be monitored, the pH of the composition of the invention will preferably be within this range, and the pH indicator and buffer will be selected to operate within the chosen range. In a preferred embodiment of this invention, the pH of the composition of the invention will be preferably within ±2 pH units of the pH of the material being monitored for freezing or thawing.

In choosing a suitable buffer system, one should not only consider the pH required, but also take into account the nature of the system in which it will be employed. The added substances must not form insoluble compounds or complexes or enter into other undesired side reactions with the medium.

It has been found that the selection of the buffer system affects the ability to regulate color change relative to the freezing point of the composition of the invention. Buffer systems based on dissociable inorganic salts having three to five ionizable groups can be employed in the invention. Such water soluble inorganic compounds having only one or two ionizable groups have not been found to be that suitable. Buffer systems based on ionizable phosphate groups have been found to be suitable. The preferred buffer system for use in the invention employs inorganic salts containing three to five ionizable phosphate groups. On the other hand, organic buffer substances and even some other inorganic buffer systems have not been found to be suitable.

Descriptions of components that make some useful phosphate buffers are:

1. Sörensen'phosphate buffer: 1/15 molar solutions of $Na_2HPO_4$ and $KH_2PO_4$ in distilled water in proportions to make up buffers of pH between 5.0 and 8.2. (Biochem. Z. 22: p 352, 1909).

2. McIlvaine's citric acid-phosphate buffer: mixture of solutions of 0.1 molar of citric acid and 0.2 molar $Na_2HPO_4$ for pH range 2.2–8.0. (J. Biol. Chem. 49: p 183, 1921).

3. Teorell and Stenhagen's citrate-phosphate-borate buffer for pH range 2.0–12.0 (Biochem Z. 299: p 416, 1938).

4. Kolthoff's borax-phosphate buffer for pH range 5.8–9.2: mixture of 0.05 molar borax and 0.1 molar $KH_2PO_4$. (J. Biol. Chem. 63: p 135, 1925).

5. Our own solutions of $Na_2 HPO_4$ and HCl or NaOH of varying molarity for the pH ranges 4.5 to 10.5.

6. Isotonic solutions used for injectable biological preparations contain in addition to secondary sodium phosphate and monopotassium phosphate, sodium chloride, magnesium chloride, and other components.

Some buffer systems have not been found to be that suitable. This supports the view that ionization in the frozen state of the buffer components is needed to effect a change in pH as evidenced by the change of color of pH indicators. (pH indicator solutions, for example, in TRIS-HCl buffer do not show any change in color upon freezing, even with added sodium chloride, which shows that pH indicators by themselves do not readily dissociate upon freezing).

The amount of buffer employed in the aqueous composition of the invention is determined based upon the desired freezing point for the composition. For lower freezing points, higher molar concentrations of the buffer salt are employed. The optimum buffer concentrations can be determined with a minimum of experimentation for the pH indicator selected by making and testing sample solutions.

The composition of the invention, as previously noted, is aqueous and a liquid at room temperature. The composition freezes when the temperature is lowered, and since the composition is useful in freeze-thaw indicators of the type depicted in the FIGURE, the freezing point of the composition is tailored to match the perishable composition being monitored. For this reason, substances that materially change the freezing point of the composition of the invention should not be added. Thus, the addition of solvents, such as alcohols, that may depress the freezing point of the composition should be avoided. On the other hand, the addition of some substances such as preservatives, and even solvents, such as small amounts of butanol, that may act as preservatives, may be desirable. Similarly, the addition of substances that may materially detract from the intensity of the color change should be avoided.

The composition of this invention can be utilized in freeze-thaw indicators operable at −25° C. or lower. Preferably, the composition of the invention is useful in the temperature range of about −4° C. to about −18° C., especially about −4° C. to about −12° C., which is the temperature range within which many vaccines and other biological materials become perishable.

The composition of this invention also includes a metal object that hastens freezing and color change of the composition. The metal object should be one that does not corrode or rust in the composition of the invention. In addition, the metal object should not adversely affect the color of the composition. Preferably, the metal object is substantially insoluable in the composition of the invention.

The nature and the amount of the metal object should not adversely affect heat transfer between the aqueous composition of the invention and the surrounding atmosphere. Thus, for example, a metal object of large mass or a metal object of high heat content that would retard warming or cooling of the composition of the invention should be avoided.

It has been found that metal balls of spherical shape are particularly suitable for use in the invention. In particular, stainless steel balls of small size were found to produce favorable results in the Examples. The size of the metal object can be adapted to the container. Stainless steel balls of about 3 mm to about 3.15 mm were used because they could easily be introduced into the container for the composition of the invention before the container was closed with a stopper. As shown in the Examples, there did not appear to be any advantage to using two of the stainless steel balls, one ball produced satisfactory freeze-thaw characteristics for the composition. This suggests that the surface area of the metal object is not critical to the success of the invention.

The stainless steel balls employed in the Examples were identified as "SKF3" and were products of SKF of Sweden. The balls were of stainless steel and comprised 1% C, 0.25% Si, 0.35% Mn, and 1.5% Cr. Stainless steel balls are also available from F.A.G. of Germany.

It will be evident from the foregoing description that another aspect of this invention involves a composition that shows a change in pH in the frozen state at or when preselected temperatures below the freezing point are exceeded as observed by color change of pH indicators. The pH change, similar to the color change, occurs in a reversible way. The metal object, such as the metal balls, for whatever reason, influence freezing more readily than other materials tested, but the change in pH and color is dependent on the composition, time, and temperature of exposure below the freezing point. Thus, it will be evident that the composition of this invention can be employed in a method to determine pH changes at subfreezing temperatures using a pH indicator to indicate that a preselected temperature below the freezing point has been exceeded as evidenced by a color change.

The following Examples are provided in order to facilitate a clear understanding of the invention.

The described tests are carried out with one buffer substance and one or two pH-indicators as examples. It is obvious that the invention can be applied to other buffer substances and one or more pH-indicators in combination in order to obtain other color changes. The size of the metal ball can also be varied depending upon the size of the container and quantity of liquid used. The metal balls, which have been found acceptable in the invention, were products from SKF. These have been used in the following Examples.

EXAMPLE 1

Additives Influence on Freezing and Color Change at −6° C.

This Example shows freezing and color change of a pH-indicator solution. Sörensens phosphate buffer solution 0.06 M pH 7.5 is diluted to 0.012 M in distilled water containing 2% 1-butanol. To this buffer solution is added bromothymol blue to a final concentration of 0.016%. This solution is designated in the following Examples as Component 1.

The solution is filled in vials, 1.5 ml per vial that has a total volume of 1.7 ml. 12 vials are used for each additive. To each vial containing Component 1 is added either one or two metal balls (3 mm diameter), aluminiumfoil (5×10 mm), steel wire (0.5×15 mm) or copper wire (0.5×15 mm) These additives are designated as Component 2. The vials are closed with plastic stoppers.

All the vials are placed at a constant air temperature of −6° C. Reading of color change and freezing were done at different times. As shown in Table 1, Component 1 does not freeze without addition of Component 2. The quickest change occurs with metal balls. Of the vials containing one metal ball, the content of 11 of 12 vials froze within one hour, whereas those having two metal balls all the 12 vial contents were in the frozen state. The color at this time is unchanged blue. After further two hours storage all the vials showed a change to yellow color. No significant difference could be observed between addition of one or two balls. With the other additives a considerably slower change happens.

EXAMPLE 2

Additives Influence on Freezing and Color Chance at −9° C.

Even in this Example are Components 1 and 2 the same as in the previous experiment. 12 vials per additive are used in the test. The additives are also the same as earlier, but the vials containing only one metal ball are not included. In this Example, the temperature was lowered to −9° C. Due to the lower temperature, observations were made during shorter times. Here, once again, addition of metal balls gave a quicker color change. All the 12 vials with metal balls gave color change within one hour. Other additives did not give early color changes and gave also more variable results. This can be observed from Table 2.

EXAMPLE 3

Experiment With 100 Vials With and Without Metal Ball at The Temperature Between −2° C. and −6° C.

200 vials were filled with Component 1. To 100 vials were added one metal ball each as Component 2, whereas the remaining 100 vials functioned as Controls. The vials were closed with plastic stoppers and placed in a frozen area. In the experiment (Table 3) the air temperature gradually fell down from −2° C. to −6° C. during a period of 23 hours. Both temperature and the samples were read at different times. As follows from the Example in Table 3, when the temperature was lowered from −2° C. to −3° C., two samples containing metal ball froze and became yellow. The controls were unchanged. When the temperature lowered to −4.5° C. the contents of 96 vials with metal ball froze, whereas 97 of the vials in the Control group were unchanged. With an additional lowering of temperature from −4.5° C. to −6° C., 96 samples containing metal ball changed to yellow color and 4 remained unchanged. On the other hand, 96 vials in the Control group were not frozen and the contents were still blue and in a liquid state. Only the content of four vials changed to yellow color.

EXAMPLE 4

Experiment With 100 Samples With and Without Metal Ball at −6° C.

The same test as under Example 3 was repeated at a constant air temperature of −6° C. The results are shown in Table 4. 75 samples with added metal ball showed freezing and color change from blue to yellow after 2 hours exposition at −6° C. 25 samples were still blue and in the liquid state. After four hours time, 90 samples with metal ball were frozen and yellow. 10 samples were still blue and the contents in the liquid state. The samples in the Control group did not, however, show any change.

EXAMPLE 5

Times for Color Chance at Different Temperatures for 6 Samples in Each Group.

The test was performed with addition of one or two metal balls. Even in this test there was a Control group. 6 vials in each group were placed in a glycol-water bath where the temperature could be regulated. The vials were exposed to different temperatures. The time when the contents in all six vials changed color from blue to yellow was noted. The observation time was 120 minutes at each temperature. The vials that contained only Component 1 (Control group) did not become yellow in color until the temperature was −12° C. On the other hand, the test samples in both the other groups changed color already at 4.5° C. No significant differences could be noticed between test materials having one or two metal balls.

EXAMPLE 6

Effect of Short Time Exposure to Freezing Temperature.

The foregoing Examples show the effect of constant freezing temperatures, on freezing and color chance. What often occurs is that cold storage products are exposed during shorter periods of time to freezing temperatures, i.e. during transportation during the winter season. In order to simulate such a situation, vials containing Component 1 containing different Component 2 additives were exposed first to an air temperature of −6° C. during one hour, and afterwards the temperature was increased successively as described in Table 6. Five vials of each were used for each Component.

The results show that neither Component 1 alone nor those with Component 2 additives, such as aluminum foil, steel wire, copper wire, or glass beads (3-mm diameter) froze under the experimental conditions. Only those with added metal ball froze and effected the change of color.

EXAMPLE 7

Effect of Buffer Molarity and pH Upon Freezing and Color Change.

In this Example are shown compositions containing 0.06, 0.012 and 0.006M phosphate buffer solutions of pH values 9.9, 9.3 and 8.7. Phenolphthalein was added as pH indicator. Vials were filled with 1.5 ml and, after adding a metal ball, closed with plastic stoppers. The samples, which were initially rose in color, were placed in a cold bath and the temperature stepwise lowered below 0° C.

As exemplified in Table 7, the composition containing pH 9.9 buffer of 0.006M froze at −3° C. and the color turned to white (colorless). Buffer compositions of 0.06 and 0.012M froze at −5° C. but without change of color. Even when the temperature was lowered down to −10° C. the color was unchanged. When the test samples were placed at −18° C. in a freezer, the color changed from rose to white in the vial containing 0.012M buffer solution. On the other hand, there was no change of color of the 0.06M buffer containing vials even when the temperature was lowered to −25° C. With samples of pH 9.3 buffer solution, the content of 0.06M buffer froze at −4° C. and the color changed to white. With lower buffer capacity, the contents of 0.012M and 0.006M froze at −5° C. and −6° C., respectively, with color change. With 0.06M buffer solution of pH 8.7 freezing occurred at −4° C. exhibiting a color change. This Example shows that different freezing points and color change temperatures can be obtained by changing the buffer molarity and pH.

EXAMPLE 8

Studies Using Preservatives.

This Example shows the effect of preservatives on freezing and change of color of phosphate buffer 0.012M, pH7.6, containing bromothymolblue (Component 1). Three different preservatives were tested, and they were compared with Controls without preservative. Test samples were filled with .5 ml of solution per vial, and after addition of metal balls, closed with plastic stoppers. They were then placed in a cold bath where the temperature was lowered stepwise. The vials were exposed for one hour at each temperature.

The results, as evident from Table 8, show that the three tested preservatives did not have any significant influence on freezing and color change.

EXAMPLE 9

Test with Ice Packs.

Among certain ice packs there was found the possibility to insert, from the outside, small containers, containing the composition of this invention with metal balls according to Example 1. We used these ice packs in the test. The ice packs were placed in freezers and observed for color change from blue to yellow. When this happened, one could verify that the temperature in the ice packs was just below −5° C. Measurement was made with the help of a temperature measuring instrument. One may thus also use ice packs much earlier than what one normally does by reading the color of the inserted container, containing the composition of the invention.

In summary, this invention provides a composition consisting essentially of a pH indicator and an inorganic buffer salt solution, which can undergo single or multiple freeze-thaw cycles. The composition of the invention can be frozen, but does not undergo a color change at its freezing point. Instead, the composition is tailored to undergo a color change at a temperature below the freezing point. While the addition of the metal object to the composition affects its freezing point by raising the temperature at which the composition will freeze, the added metal object has not been found to alter the color change. The color change is based on the pH and ion concentration of the buffer solution and the pH indicator or mixture of indicators in the composition. Indeed, there does not appear to be any relationship between the metal object and the color change observed.

This combination of properties makes the composition of the invention well suited for freeze-thaw indicators, particularly indicators for monitoring perishable goods, such as vaccines, biological products, and agricultural products. Freeze-thaw monitors of the invention are provided by introducing the composition of the invention into suitable container provided with a closure means, such as a stopper or cover.

TABLE 1

Additives' influence on freezing and on color change at −6° C.

| Time. hour | Air temp. ° C. | Component 1 | Component 1 +1 metal ball | Component 1 +2 metal-balls | Component 1 + Al-foil | Component 1 + steel wire | Component 1 + Cu-wire |
|---|---|---|---|---|---|---|---|
| Start 12.45 | −6 | Blue, liquid | Blue, liquid | Blue, liquid | Blue, liquid | Blue, liquid | Blue, liquid |
| Read 14.45 | −6 | " | 11 blue. frozen 1 blue, liquid | 12 blue, frozen | " | " | " |
| Read. 15 45 | −6 | " | 11 blue. frozen 1 blue, liquid | 12 blue, frozen | " | 2 blue, frozen 10 blue liquid. | " |
| Read 16.30 | −6 | " | 3 yellow. frozen 9 blue. frozen | 3 yellow. frozen 9 blue frozen | 5 yellow. frozen 7 blue frozen | 1 yellow. frozen 11 blue frozen | " |
| Read 17.00 | −6 | " | All yellow. frozen | All yellow. Frozen | 5 yellow. frozen 7 blue frozen | 1 yellow. frozen 11 blue frozen | " |
| Read 17.45 | −6 | " | All yellow. frozen | All yellow. Frozen | 5 yellow. frozen 7 blue frozen | 1 yellow. frozen 11 blue frozen | " |

TABLE 2

Additives' influence on freezing and on color change at −9° C.

| Time. hour | Air temp. ° C. | Component 1 | Component 1 +2 metal balls | Component 1 + Al.foil | Component 1 + steel wire | Component 1 + Cu. wire |
|---|---|---|---|---|---|---|
| Start 14.50 | −9 | Blue. liquid | Blue. liquid | Blue. liquid | Blue. liquid | Blue. liquid |
| Read 15.20 | " | 1yellow. frozen 11 blue. liquid | 2 yellow. frozen 10 blue, liquid | " | 1 yellow. frozen 11 blue, liquid | " |
| Read 15.35 | " | 1yellow. frozen 11 blue. liquid | 5 yellow frozen 7 blue liquid | 1 yellow frozen 11 blue liquid | 5 yellow frozen 7 blue liquid | 4 yellow. frozen 8 blue liquid |
| Read 15.40 | " | 1yellow. frozen 11 blue. liquid | 9 yellow. frozen 3 blue. liquid | 1 yellow frozen 11 blue liquid | 7 yellow. frozen 5 blue. liquid | 4 yellow. frozen 8 blue liquid |
| Read 15.45 | " | 1yellow. frozen 11 blue. liquid | 12 yellow. frozen | 1 yellow frozen 11 blue liquid | 7 yellow. frozen 5 blue. liquid | 4 yellow. frozen 8 blue liquid |
| Read 15.55 | " | 1yellow. frozen 11 blue. liquid |  | 1 yellow frozen 11 blue liquid | 8 yellow. frozen 4 blue. liquid | 4 yellow. frozen 8 blue liquid |
| Read 16.00 | " | 1yellow. frozen 11 blue. liquid |  | 2 yellow. frozen 10 blue. liquid | 10 yellow. frozen 2 blue. liquid | 5 yellow. .frozen 7 blue. liquid |
| Read 16.05 | " | 3 yellow. frozen 9 blue liquid |  | 2 yellow. frozen 10 blue. liquid | 11 yellow. frozen 1 blue liquid | 5 yellow. .frozen 7 blue. liquid |
| Read 16.10 | " | 3 yellow. frozen 9 blue liquid |  | 3 yellow. frozen 9 blue liquid | 11 yellow. frozen 1 blue liquid | 5 yellow. .frozen 7 blue. liquid |
| Read 16.30 | " | 3 yellow. frozen 9 blue liquid |  | 4 yellow. frozen 8 blue liquid | 11 yellow. frozen 1 blue liquid | 6 yellow. froze 6 blue liquid |

TABLE 3

Experiment with 100 samples with and without metal ball at temperatures between −2 and −6° C.

| Reading time from start hours | Air temp. ° C. | Component 1 (control) | Component 1 + metal ball |
|---|---|---|---|
| 0 | −2 | Blue. liquid | Blue. liquid |
| 8 | −3 | -"- | 2 yellow. frozen 98 blue. liquid |
| 22 | −4.5 | 3 yellow. frozen 97 blue liquid | 2 yellow. frozen 94 blue frozen 4 blue. liquid |
| 23 | −6 | 4 yellow. frozen 96 blue liquid | 96 yellow. frozen 4 blue. liquid |

TABLE 4

Experiment with 100 samples. with and without metal ball. Temperatur −6° C.

| Time. hours | Air temp.° C. | Component 1 | Component 1 + metal ball |
|---|---|---|---|
| Start. 0 | −6 | 100 blue. liquid | 100 blue. liquid |
| 2 | −6 | -"- | 75 yellow. frozen 25 blue. liquid |
| 4 | −6 | -"- | 90 yellow frozen 10 blue. liquid |

TABLE 5

Time for color change at different temperatures. for six samples in every group.

| Temp.° C. Cold bath | Component 1 (control) | Component 1 + 1 metal ball | Component 1 + 2 metal balls |
|---|---|---|---|
| −3 | >120 minutes | >120 minutes | >120 minutes |
| −4.5 | -"- | 90 minutes | 90 minutes |
| −5 | -"- | 38 minutes | 30 minutes |
| −6 | -"- | 30 minutes | 30 minutes |
| −7 | -"- | 15 minutes | 15 minutes |
| −8 | -"- | 12 minutes | 15 minutes |
| −10 | -"- | 8 minutes | 8 minutes |
| −12 | 60 minutes | 5 minutes | 5 minutes |

TABLE 6

Influence of short-term exposition to freeze temperature.

| Time hour. | Air temp. ° C. | Component 1 | Component 1 + metal ball | Component 1 + Al.foil | Component 1 + steel wire | Component 1 + Cu. wire | Component 1 + glass bead |
|---|---|---|---|---|---|---|---|
| Start 10.10 | −6 | Blue. liquid | Blue. liquid | Blue. liquid | Blue. liquid | Blue. liquid | Blue, liquid |
| Read 11.10 | −5 | " | " | " | " | " | " |
| Read 12.20 | −4 | " | 4 blue. frozen 1 blue. liquid | " | " | " | " |
| Read 16.10 | −3 | " | 5/5 yellow. frozen | " | " | " | " |
| Read 18.10 | −2 | " | 5/5 blue. frozen | " | " | " | " |
| Read 21.10 | 0 | " | 4 blue. frozen 1 blue. liquid | " | " | " | " |

TABLE 7

Influence of buffers molarity and pH on freezing and color change.

| Temp. ° C. | pH 9.9 buffer | | | pH 9.3 buffer | | | pH 8.7 buffer |
|---|---|---|---|---|---|---|---|
| Cold bath | 0.06M | 0.012M | 0.006M | 0.06M | 0.012M | 0.006M | 0.06M |
| −1 | Rose. liquid | Rose. liquid | Rose. liquid | Rose. liquid | Rose. liquid | Rose. liquid | Rose. liquid |
| −2 | " | " | " | " | " | " | " |
| −3 | " | " | White. frozen | " | " | " | " |
| −4 | " | " | | White, frozen | " | " | White, frozen |
| −5 | Rose. frozen | Rose. frozen | | | White, frozen | " | |
| −6 | " | " | | | | White, frozen | |
| −7 | " | " | | | | | |
| −8 | " | " | | | | | |
| −9 | " | " | | | | | |
| −10 | " | " | | | | | |
| Freezer −18 | " | White. frozen | | | | | |
| Freezer −25 | " | | | | | | |

TABLE 8

Experiment with preservative.

| Temp ° C. Cold-bath | Component 1 +metal ball | Component 1 +metal ball +Sodium. benzoate | Component 1 +metal ball +Quaternary ammonium salts | Component 1 +metal ball +1-Butanol |
|---|---|---|---|---|
| −2 | Blue, liquid | Blue, liquid | Blue-green, liquid | Blue, liquid |
| −3 | " | " | " | " |
| −4 | " | Yellow frozen | " | " |
| −5 | Yellow, frozen | | Yellow, frozen | Yellow, frozen |

Sodium benzoate 0.05%, Quaternary ammonium salts 0.01%, 1-Butanol 2%–4% used at final concentration.

What is claimed is:

1. Composition consisting of two components, which together show an elevated freezing point and bring about color change at selected freeze temperatures, wherein the composition consists of Component 1 consisting of a buffer solution containing at least one pH indicator and Component 2 consisting of a solid material in the form of a metal object, which hastens freezing and color change.

2. Composition according to claim 1, wherein a preservative is added to Component 1 and the preservative is selected from the group consisting of butanol, quaternary ammonium salts, and sodium benzoate.

3. Composition according to claim 1, wherein Component 2 is metal wire or metal balls.

4. Method for preparation of the composition according to claim 1 having a regulated color change and freezing at selected temperatures in order to show that a certain temperature interval has been exceeded or fallen below, wherein the method comprises providing Component 1 consisting of an aqueous buffer solution and at least one pH indicator, and adding Component 2 to Component 1, wherein Component 2 consists of a metal object.

5. Method of preparation of the composition according to claim 4, wherein a preservative is added to Component 1, and the preservative is selected from the group consisting of butanol, quaternary ammonium salts, and sodium benzoate.

6. Method of preparation of the composition according to claim 4, wherein Component 2 is metal wire or metal balls.

7. A temperature indicating device comprising the composition according to claim 1, wherein the said composition is in a transparent container of plastic or glass and with a background of a color, a number, or letter, which makes it possible to observe any difference in color change.

8. The device according to claim 7, wherein the device is a freeze-warning device.

9. The device according to claim 7, wherein the device is a thaw indicator for frozen products that should not thaw during storage and handling.

10. The device according to claim 7, wherein the composition is enclosed in transparent ice packs or in the form of a container inserted from the outside of the ice packs.

11. A device comprising a composition in a frozen state, wherein the composition comprises two components, which together show an elevated freezing point and bring about color change in the composition at selected freeze temperatures below the freezing point of the composition in a reversible way in order to show if a predetermined temperature limit has been exceeded or fallen below, wherein the composition comprises:

(a) a buffer solution containing at least one pH-indicator; and (b) at least a solid material in the form of a metal object, which does not corrode or rust and which hastens freezing and color change in the composition when the composition is lowered in temperature to the frozen state;

wherein the composition is in a container of plastic or glass.

12. A device comprising a composition, which comprises two components, which together show an elevated freezing point and bring about, in the frozen state, a color change in the composition at predetermined freeze temperatures below the freezing point of the composition in a reversible way in order to show if a set temperature limit has been exceeded or fallen below, wherein the composition comprises:

(a) a buffer solution containing at least one pH-indicator; and (b) at least a solid material in the form of a metal object, which does not corrode or rust and which hastens freezing and color change in the composition when the composition is lowered in temperature;

wherein the composition is enclosed in a transparent container of glass or plastic.

13. A device comprising a composition consisting of two components, which together show an elevated freezing point and bring about color change at selected freeze temperatures below the freezing point of the composition in a reversible way in order to show if a set temperature limit has been exceeded or fallen below, wherein the composition consists of:

(a) a buffer solution containing at least one pH indicator; and (b) a solid material in the form of a metal object, which does not corrode or rust and which hastens freezing and color change in the composition;

wherein the composition is enclosed in a transparent container of glass or plastic.

* * * * *